United States Patent
Eide

(10) Patent No.: US 9,867,897 B2
(45) Date of Patent: Jan. 16, 2018

(54) ACTIVE PHOTOCATALYTIC OXIDATION

(71) Applicant: DBG GROUP INVESTMENTS LLC, Dallas, TX (US)

(72) Inventor: Andrew Eide, Rockwall, TX (US)

(73) Assignee: DBG Group Investments LLC, Dallas, TX (US)

( * ) Notice: Subject to any disclaimer, the term of this patent is extended or adjusted under 35 U.S.C. 154(b) by 301 days.

(21) Appl. No.: 14/705,046

(22) Filed: May 6, 2015

(65) Prior Publication Data

US 2015/0231298 A1 Aug. 20, 2015

Related U.S. Application Data

(63) Continuation-in-part of application No. 13/602,102, filed on Sep. 1, 2012, now Pat. No. 9,623,374.

(51) Int. Cl.
  *A61L 9/20* (2006.01)
(52) U.S. Cl.
  CPC ..................... *A61L 9/205* (2013.01)
(58) Field of Classification Search
  CPC . A61L 2/20; A61L 2/205; A61L 2/088; A61L 2/10; A61L 9/205; A61L 2209/212
  See application file for complete search history.

(56) References Cited

U.S. PATENT DOCUMENTS

| | | |
|---|---|---|
| 8,658,101 B1 | 2/2014 | Burnett |
| 9,011,780 B1 | 4/2015 | Burnett |
| 2006/0262389 A1 | 11/2006 | Zaczek |
| 2009/0041617 A1 | 2/2009 | Lee |
| 2012/0315184 A1 | 12/2012 | Clark |
| 2014/0050611 A1* | 2/2014 | Warren .................. A61L 9/205 422/4 |
| 2014/0065023 A1 | 3/2014 | Eide |
| 2014/0091230 A1 | 4/2014 | Clark et al. |

OTHER PUBLICATIONS

PCT: International Search Report and Written Opinion of PCT/US15/33364 (related application); Sep. 4, 2015; 16 pgs.

* cited by examiner

*Primary Examiner* — Timothy C Cleveland
(74) *Attorney, Agent, or Firm* — Munck Wilson Mandala, LLP

(57) ABSTRACT

An active oxidation and purifying system is provided to increase or maximize the rate of photocatalytic oxidation and ambient air purification capacity by providing both direct ultraviolet (UV) light and reflected UV light directed to the surface and apertures of active cell panels coated with a photocatalytic material. In one example, the active cells also include a plurality of apertures disposed in a transverse manner from the first surface to the second surface of the active cell. Furthermore, a first set of the apertures could be disposed about 45 degrees relative to a median axis along the first and second surfaces, while a second set of apertures could be disposed about negative 45 degrees relative to the same median axis in order to increase the surface area impinged by the direct and reflected UV light.

10 Claims, 14 Drawing Sheets

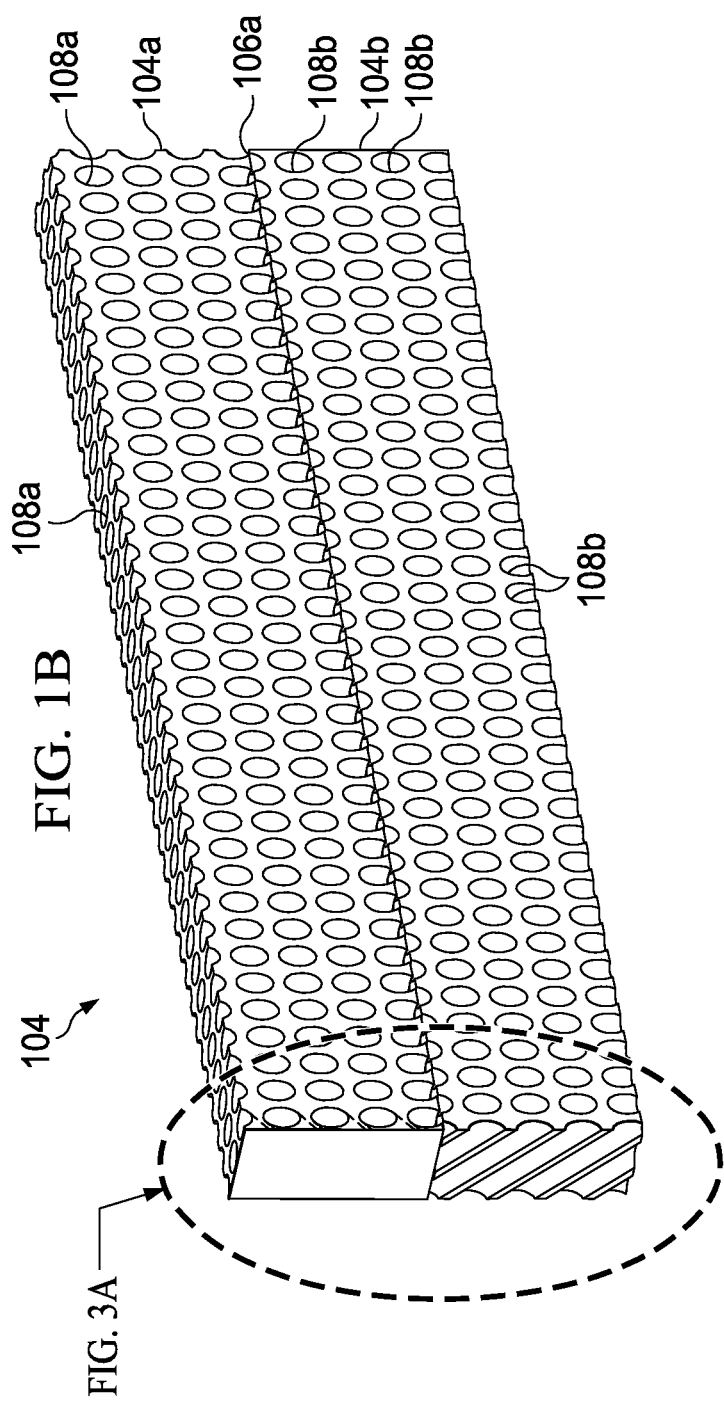

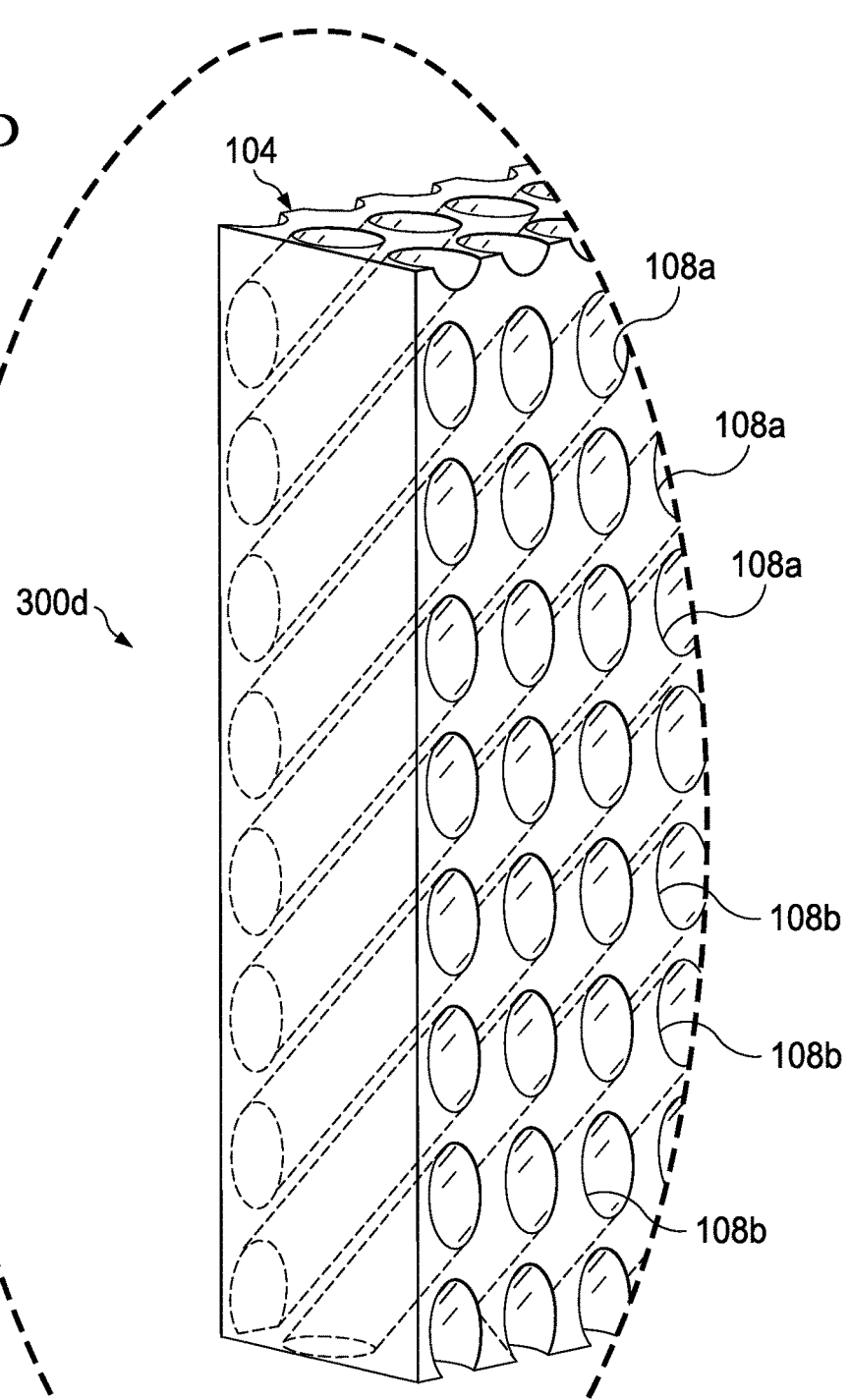

ACTIVE PHOTOCATALYTIC OXIDATION

CROSS-REFERENCE TO RELATED APPLICATIONS

This application is a continuation-in-part of U.S. patent application Ser. No. 13/602,102, filed Sep. 1, 2012, entitled ACTIVE PHOTOCATALYTIC OXIDATION, the specification of which is incorporated by reference herein in its entirety.

TECHNICAL FIELD

The present disclosure relates generally to air filtering or purifying systems and, in particular, to systems and methods of using ultraviolet light to oxidize and purify the ambient environment using photocatalytic oxidation.

BACKGROUND

Conventional systems, such as high-efficiency particulate air (HEPA) filtration systems, require contaminates to come in direct contact with a filter to remove such contaminants and fail to address any surface contaminants. Other conventional systems using ultraviolet light to oxidize ambient air typically use particle filters that, when energized by a centrally located ultraviolet (UV) light source, aid in purifying the ambient air and environment by converting toxic compounds to benign constituents. Such systems typically include rows of coated particle filters that form a structure to selectively envelope the UV light source. The UV light in such systems fails to adequately expose the surfaces of conventional particle filters to the UV light and, thus, such systems typically yield rates of photocatalytic oxidation and air filtration that are relatively low.

What is needed, is an effective and efficient system of increasing the rate of photocatalytic oxidation to ultimately increase the rate and efficiency of oxidizing and purifying the ambient environment.

SUMMARY

Embodiments of the present disclosure generally provide systems and methods of using ultraviolet light and photocatalytic oxidation to oxidize and purify the ambient environment.

In one embodiment a photocatalytic oxidation system is provided that comprises a housing. The housing comprising a proximate end panel and a distal end panel. The housing has a longitudinal direction extending from the proximate end panel to the distal end panel. The housing further includes an upper panel extending between top sides of both the proximate end panel and the distal end panel. There is a lower panel extending between lower sides of both the proximate end panel and the distal end panel. The lower panel is spaced from the upper panel. A first active cell panel extends between a first side of the proximate end panel, a first side of the distal end panel, a first side of the upper panel, and a first side of the lower panel. The active first cell comprises a first plurality of apertures disposed in a transverse manner extending from an inner side to an outer side of the first active cell panel.

Additionally, a second active cell panel extends between a second side of the proximate end panel, a second side of the distal end panel, a second side of the upper panel, and a second side of the lower end panel. The second active cell comprises a second plurality of apertures disposed in a transverse manner extending from an inner side to an outer side of the second active cell panel.

There is an interior chamber bounded by the proximate end and distal end panels, the upper and lower panels, and the first and second active cell panels. An elongate UV bulb is positioned inside the interior chamber and has a center axis that is parallel with the longitudinal direction.

The embodiment further includes a first reflective feature that protrudes inward into the interior chamber from an inner surface of the upper panel. The first reflective feature further extends in the longitudinal direction on the inner surface of the upper panel and is configured to reflect ultraviolet (UV) radiation emitted radially from the elongate UV bulb toward the first plurality of apertures and the inner side of the first active cell, as well as toward the second plurality of apertures and the inner side of the second active cell.

Embodiments may include a first reflective feature that comprises a convex protrusion into the interior chamber from the inner surface of the upper panel.

The first reflective feature may be a V-shape in cross section. And, may additionally be configured to provide stiffening and structural support to the housing.

In various embodiments the inner side and/or the surfaces of the first plurality of apertures of the first active cell panel are coated with a photocatalytic material.

In various embodiments the first reflective feature is provided over a portion of an entire longitudinal length of the upper panel.

Additionally, in some embodiments a center longitudinal axis of the first reflective feature is aligned with the center axis of the elongate UV bulb.

In various embodiments, the reflective feature comprises a metal UV reflective surface.

Additionally, some embodiments further comprise a second reflective feature that protrudes inward into the interior chamber from an inner surface of the lower panel. The second reflective feature is provided in the longitudinal direction on the inner surface of the lower panel and is configured to reflect UV radiation, which is emitted radially from the elongate UV bulb toward the lower panel, toward the first plurality of apertures and the inner side of the first active cell, as well as toward the second plurality of apertures and the inner side of the second active cell.

Another embodiment of a photocatalytic oxidation system comprises an inner cavity; an elongate UV bulb having a central axis in a longitudinal direction and positioned in the inner cavity; and first and second active cell panels positioned on opposing sides of the inner cavity and each being parallel with the central axis of the elongate UV bulb. The first and second active cell panels each comprise an inner surface that faces the inner cavity. Each of the inner surfaces of the first and second active cell panels are coated with a photocatalytic material configured to exhibit a photocatalytic oxidative process when subjected to UV radiation emitted from the elongate UV bulb. There is also an upper side panel that extends between upper edges of the first and second active cell panels. The upper side panel comprises an upper reflective feature that includes an upper convex protrusion that protrudes from an inner surface of the upper side panel inward into the inner cavity. The upper reflective feature extends longitudinally on the inner surface of the upper side panel and has a cross section that is a mirror image about a central longitudinal and vertical plane through the upper convex protrusion. The surface of the reflective feature is configured to reflect UV radiation emitted from the elongate UV bulb in the direction of the upper side panel toward both the inner surfaces of the first and second active cell panels. Additionally, a bottom side panel extends between lower edges of the first and second active cell panels.

In various embodiments the first and second active cell panels each further comprise a plurality of apertures disposed in a transverse manner from the inner surface to the outer surface of the first and second active cell panels, and the aperture surfaces are each coated with the photocatalytic material and configured to allow airflow there through.

In other embodiments the bottom side panel may further comprise a lower reflective feature that includes an upper convex protrusion that protrudes from an inner surface of the lower side panel inward into the inner cavity, the lower reflective feature extends in a longitudinal direction on the inner surface of the lower side panel and has a cross section that is a mirror image about a central longitudinal vertical plane through the lower convex protrusion. The surface of the reflective feature is configured to reflect UV radiation emitted from the elongate UV bulb in the direction of the lower side panel toward both the inner surfaces of the first and second active cell panels.

In some embodiments, the cross section of the upper convex protrusion is a V-shape.

In various embodiments, the plurality of apertures transverse from the inner surface to the outer surface of the first and second active cell panels in a diagonal manner.

In some embodiments, the upper reflective feature extends the entire longitudinal length of the upper side panel.

Other technical features may be readily apparent to one skilled in the art from the following figures and descriptions.

BRIEF DESCRIPTION OF THE DRAWINGS

For a more complete understanding of this disclosure and its features, reference is now made to the following description, taken in conjunction with the accompanying drawings, in which:

FIGS. 1A and 1B are perspective views of an active photocatalytic oxidation system having an active cell in accordance with an embodiment of the present disclosure;

FIGS. 3A-3D are partial cross sectional views of the system embodiment shown in FIGS. 1A, 1B and 2;

DETAILED DESCRIPTION

The present disclosure relates generally to air purifications systems methods and methods, in particular, to systems and of using ultraviolet light and photocatalytic oxidation to oxidize and purify the ambient environment. Embodiments of air purification systems in accordance with the invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey pertinent aspects of the invention to those skilled in the art.

An embodiment of a photocatalytic oxidation system could include an active cell having multiple rows of selectively arranged specially treated and coated cell apertures that, when energized by light emitted from a centrally located ultraviolet (UV) light source, aid in oxidizing and purifying the ambient air, surrounding active cell surfaces or ambient environment by converting toxic compounds to benign constituents and controlling or neutralizing contaminants in the ambient environment. The multiple rows of cell apertures could form a honeycomb-like, array or other suitable structures selectively positioned to envelope or at least partially surround the UV light source. By selectively positioning the cell apertures to maximize UV exposure, the active cell increases the relative rates of photocatalytic oxidation and purification when compared to conventional oxidation systems, purification systems, or particle filters. Additionally, by including additional strategically placed angled reflective surfaces within a structure surrounding the UV light source, additional UV light emitted from the UV light source can be reflected from the interior reflective surfaces towards the active cells surfaces to further increase the efficiency of the photocatalytic oxidation and purification of, for example, air, being moved through the photocatalytic oxidation system.

Figure 1A:
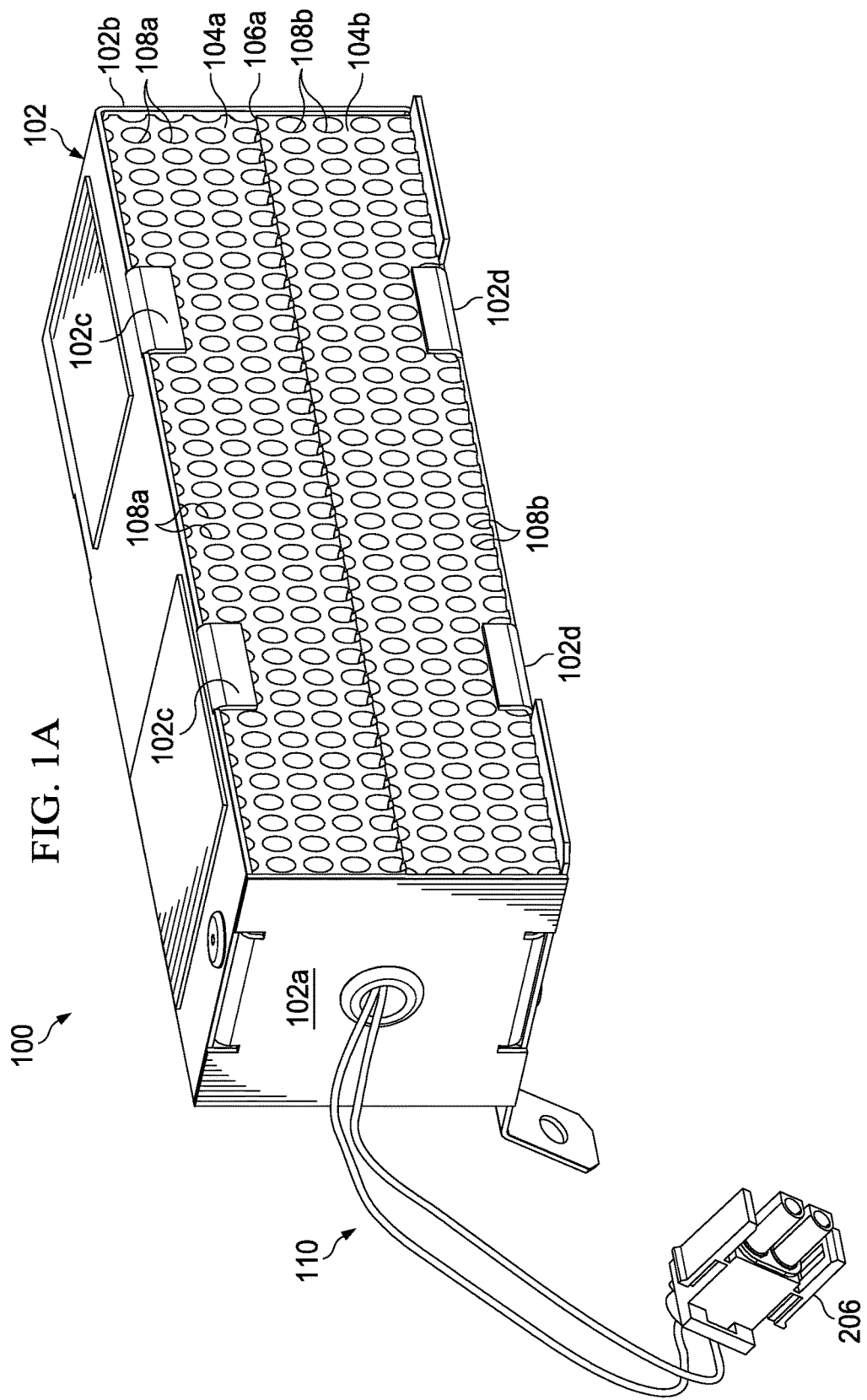

FIGS. 1A and 1B are perspective views of an embodiment of a photocatalytic oxidation system 100. Here, the photocatalytic oxidation system 100 could include housing 102, active cells 104, medians 106, cell apertures 108, and lighting assembly 110 as generally shown in FIGS. 1A and 1B and described in further detail herein. It should be understood that system 100 and active cell 104 could also include, for example, any suitable purification particle filtering system, system, oxidation active cell system, photocatalytic system, neutralizing systems, air filtration system, or combination thereof. It should also be understood that system 100 and active cell 104 shown in FIGS. 1A and 1B are for illustrative purposes only and that other suitable systems or subsystems could be used in conjunction with or in lieu of system 100 or active cell 104 and their various embodiments.

Housing 102 could include any suitably sized, shaped or configured frame, frame-like structure, housing, or housing-like structure to aid in maintaining a particular configuration of two or more active cells 104 relative to each other. The housing 102 could be coupled to or include a proximate end 102*a*, a distal end 102*b*, and side ends having lips 102*c*, 102*d*, 102*e* and 102*f* (note that lips 102*e* and 102*f* are hidden in the views shown). In various embodiments, the housing 102 could be about 5 to 20 inches in length from the proximate end 102*a* to the distal end 102*b*.

The proximate end 102*a*, distal end 102*b*, and side edges, which have elongated retaining lips 102*c*, 102*d*, 102*e* and 102*f* are collectively referred to herein as housing 102. It should be understood that housing 102 could be constructed of any suitable material such as a metallic material, plastic material, a polymer, or any suitable combination thereof and include any number of suitable labels, constructs, attachments, binding materials, and accessory like elements. It should also be understood that housing 102 or parts of housing 102 may be constructed or assembled in any suitable manner including, for example, by tabs, screws, rivets, bolts, connectors, tight fits, tapes, adhesives, magnets, sleeves, other securing or retaining mechanisms, or any combination thereof.

In various embodiments, lips 102c, 102d, 102e and 102f aid in retaining the active cells 104a, 104b, 104c, and 104d (collectively, referred to herein as active cells 104) in a particular fashion relative to each other and within the system 100. Active cells 104 could include any shaped or configured frame, structure, frame-like structure, housing, housing-like structure, or any combination thereof. Active cells 104 could include a first side exposed to an ambient environment outside of the photocatalytic oxidation system and a second side exposed to the interior chamber of the photocatalytic oxidation system 100.

Active cells 104a and 104b shown in FIG. 1A could be included as a unitary structure or as two or more separate structures. Similarly, active cells 104c and 104d shown in FIG. 1B could be included as a unitary structure or as two or more separate structures. In one embodiment, active cells 104 could be about 5 to about 20 inches in length. In one embodiment, active cells 104a and 104b could be disposed adjacent to one another along the median 106a as shown in FIGS. 1A and 1B. Likewise, active cells 104c and 104d (which are hidden in FIG. 1A) could be disposed adjacent to one another along a median 106b (also hidden in FIG. 1A. Medians 106a and 106b can be collectively referred to herein as medians 106.

In various embodiments, each of the active cells 104 could include any suitable number, size, shape, or configuration of pass-through structures or apertures such as, for example, cell apertures 108a, 108b, 108c, and 108d as generally shown in FIGS. 1A and 1B. Cell apertures 108a, 108b, 108c and 108d (and any other cell apertures included in the active cells 104) are collectively referred to herein as cell apertures 108. Cell apertures 108 could include any suitably sized, shaped or configured structure to allow ambient airflow from the outside of system 100 to pass through to an internal area of system 100 and vice versa according to one embodiment of the present disclosure.

In various embodiments, cell apertures 108 could be arranged in multiple rows, in a somewhat honeycomb-like structure or array of apertures or tube-like structures. Each of the cell apertures 108 could be disposed in a transverse or diagonal fashion relative to the housing 102 or medians 106, rather than disposed in a relatively parallel or perpendicular fashion relative to housing 102 or medians 106. As an example, each of cell apertures 108 could be transversely disposed about 45 degrees (plus or minus 20 degrees) relative to medians 106 according to one embodiment of the present disclosure.

In various embodiments, the cell apertures 108a in the active cell 104a could be disposed about +45 degrees (plus or minus 20 degrees) relative to an x-axis of median 106a, while the cell apertures 108b in the active cell 104b could be disposed about −45 degrees (plus or minus 20 degrees) relative to the same x-axis of median 104a. The, cell apertures 108c in active cell 104c could be disposed at about +45 degrees (plus or minus 20 degrees) relative to an x-axis of median 106b, while the cell apertures 108d in active cell 104d could be disposed about −45 degrees (plus or minus 20 degrees) relative to the same x-axis of median 106b.

In other embodiments, the cell apertures 108 could be positioned between about plus or minus 20 degrees and 75 degrees relative to medians 106. In still other embodiments, the optimal disposition of cell apertures 108 could be about plus or minus 45 degrees relative to medians 106. One reason for transversely or diagonally disposing the cell apertures 108 is to maximize the amount of UV light emitted from a centrally located UV light source that will impinge on the surfaces of the active cells 104 and the apertures 108 integrated in the active cells.

Figure 2:
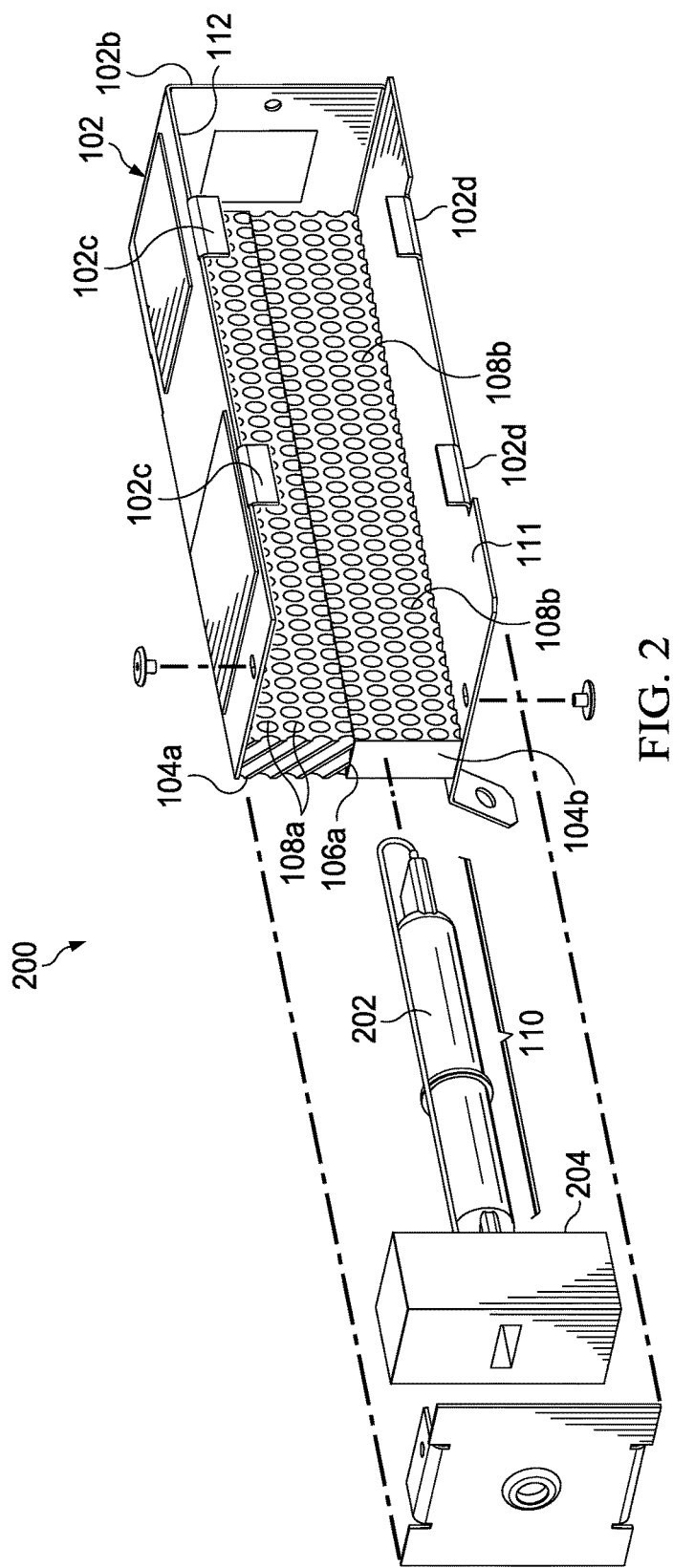
FIG. 2 is an exploded view of the system shown in FIGS. 1A and 1B according to an embodiment of the present disclosure.

FIG. 1A also depicts a lighting assembly 110 that is connected to a connector 206 at one end and adapted to receive power to energize the UV lighting assembly positioned inside the housing as shown in FIG. 2.

The active cells 104, cell apertures 108, or any combination thereof could be uniformly or selectively coated or treated with one or more photocatalytic materials, such as titanium dioxide and similar compounds. The active cells 104 that are treated with such photocatalytic materials and energized by receiving UV light emitted from a centrally located UV light source, operate by supporting a photocatalytic oxidation process that aides in the purification of the ambient air about the active cells by converting toxic compounds, via oxidation, to benign constituents. In one embodiment, active cells 104, cell apertures 108, or any suitable combination thereof may be coated with a suitable hydrophilic photocatalytic coating having non-nano titanium dioxide with several transition elements added to the coating to enhance or help optimize the overall photocatalytic effect.

FIG. 2 is an exploded view of assembly 200 of an embodiment of system 100. It should be understood that assembly 200 shown in FIG. 2 is for illustrative purposes only and that other suitable views, systems or subsystems could be used in conjunction with 100. Additionally, only a single active cell 104 wall (104a, 104b) is shown and a second active cell 104 wall (104c, 104d) is left out of the figure to make the interior of the assembly 200 easier to view.

In various embodiments, assembly 200 shown in FIG. 2 generally illustrates an embodiment of an unassembled portion of system 100 shown in FIGS. 1A and 1B. Here additional subassemblies and parts of the embodiment are shown to include a UV light source 202, and a spacer 204. As illustrated by FIGS. 1A and 2, when system 100 is fully assembled UV light source 202 is disposed between active cells 104a, 104b, 104c, and 104d according to one embodiment of the present disclosure such that the when the UV light source 202 emits UV light, the UV light impinges on the active cell surfaces facing the interior of the housing. Additionally, the UV light impinges on the interior surfaces of the lower and upper housing panel surfaces 111, 112. In various embodiments the lower and upper housing panel surfaces 111, 112 are reflective surfaces that reflect UV light emitted from the UV light source 202 back toward the UV light and toward the inner surfaces of the active cell 104a and the plurality of interior surfaces of the cell apertures 108a, 108b. In order to be reflective surfaces, the inner surfaces of the housing panels 111, 112 can have their surfaces buffed, have a reflective coating placed thereon, or be made of a material, such as aluminum, stainless steel, certain types of plastic/polymers or other materials that reflect UV light. The reflective surfaces of the inner surfaces of the lower and upper housing panels are provided to reflect UV light emitted from the UV light source 202 onto and into the aperture surfaces of the apertures 108 thereby enhancing the efficiency of the photocatalytic oxidation reaction and air cleaning capability of the system 100.

In various embodiments, the UV light source 202 could include any suitably sized, shaped, or configured UV light source, UV lamp, UV bulb, UV light emitting diode array, other suitable sources of UV or UV subtype C (UVC) radiation, or any combination thereof providing a suitable amount of UV intensity to activate the coating on the active cells 104. The UV light source 202 is configured to provide UV light of sufficient intensity to induce photocatalytic oxidation of coating or the treatment applied to the surface of the active cells 104. In various embodiments the UV light source 202 includes, for example, a UV light source having a wavelength of 185 nanometers (nm) or 254 or a broad spectrum lamp capable of providing UV light providing both wavelengths of 185 nm and 254 nm to induce photocatalytic oxidation of active cells 104.

When system 200 is assembled, the spacer 204, which is part of the lighting assembly 110, aids in maintaining the relative central-axial position of UV light source 202 within housing 102. Although a particular configuration of spacer 204 is shown in FIG. 2, it should be understood that spacer 204 could include any suitable size, shape, or configuration to maintain the relative position of the UV light source inside the housing with respect to the active cells 104. In various embodiments, spacer 204 could also be used to maintain the relative position of the lighting assembly 110 relative to housing 102 and connector 206 as generally shown in FIG. 2.

The connector 206 can be part of the lighting assembly 110 and is electrically coupled with UV light source 202. Connector 206 can include any suitable connection to a power source (not shown) for powering the lighting assembly 110. Connector 206 could include any suitably sized, shaped, or configured connector including, for example, any suitable multiple pin connector with two or more electrical contacts.

As illustrated by FIG. 2, when assembly 200 is fully assembled, the UV light source 202 is disposed centrally within the housing chamber and between the active cells 104a, 104b, 104c, and 104d. Although active cells 104 are disposed opposite from one another relative to UV light source 202, it should be understood that the relative positions and configurations of active cells 104 could be varied in other suitable manners. The UV light source is configured to emit light radially outward from the surface of the UV light source such that the emitted UV light impinges on the exposed surfaces of the active cells 104 that are facing the UV light source.

For example, the active cells 104 could be disposed in three sides or as three walls of the housing 102 and about the chamber within. In another example, the active cells 104 could be disposed in a triangular manner encasing or substantially surrounding UV light source 202. In another example, the active cells 104 could be disposed in a box-like manner encasing or substantially surrounding the entire perimeter of the chamber within the housing and about the UV light source 202 according to another embodiment. As still another example, active cells 104 could be disposed in a circular manner encasing or substantially surrounding UV light source 202 in another embodiment.

FIGS. 3A, 3B, 3C and 3D are somewhat simplified partial cross sectional views 300a, 300b, 300c and 300d (collectively referred to herein as views 300) of exemplary active cells 104 in accordance with embodiments of the present disclosure. It should be understood that views 300 shown in FIGS. 3A-3D are for illustrative purposes only and that any other suitable view, system or subsystem could be used in conjunction with or in lieu of active cells 104 shown in views 300 according to one embodiment of the present disclosure.

Figure 3A:
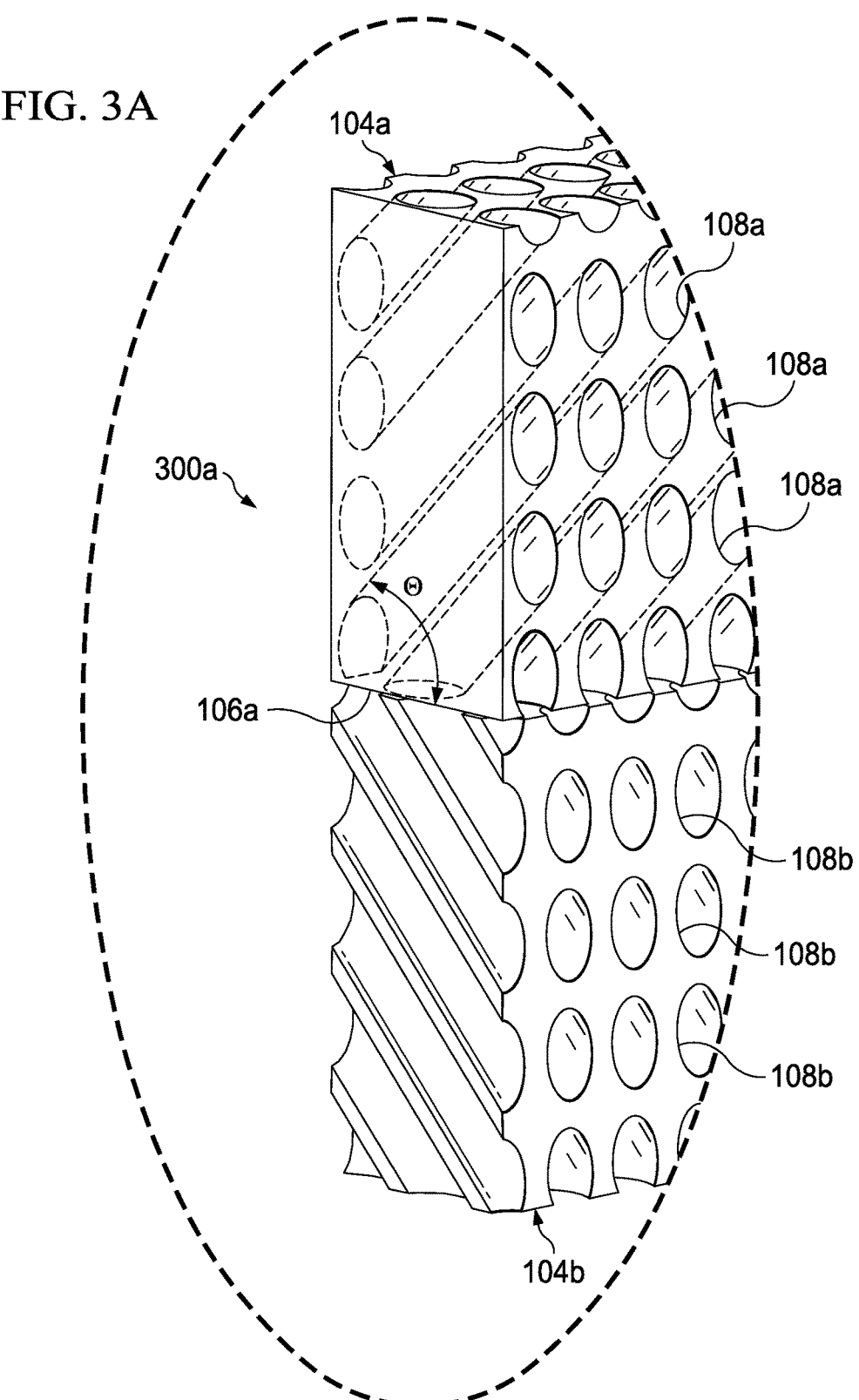

In the embodiment shown in FIG. 3A, active cells 104a and active cells 104b are structurally independent from each other. Cell apertures 108a in active cell 104a could be disposed in a transverse direction about minus θ degrees relative to an x-axis of median 106a, while cell apertures 108b in active cell 104b could be disposed about positive θ degrees relative to the same x-axis of median 106a as shown in FIG. 3A. In an exemplary embodiment, active cell 104a and active cell 104b are structurally independent from each other. The cell apertures 108a in active cell 104a could be disposed in a transverse direction about minus 45 degrees (plus or minus 20 degrees) relative to an x-axis of median 106a, while cell apertures 108b in active cell 104b could be disposed about positive 45 degrees (plus or minus 20 degrees) relative to the same x-axis of median 106a as shown in FIG. 3A.

Figure 3B:
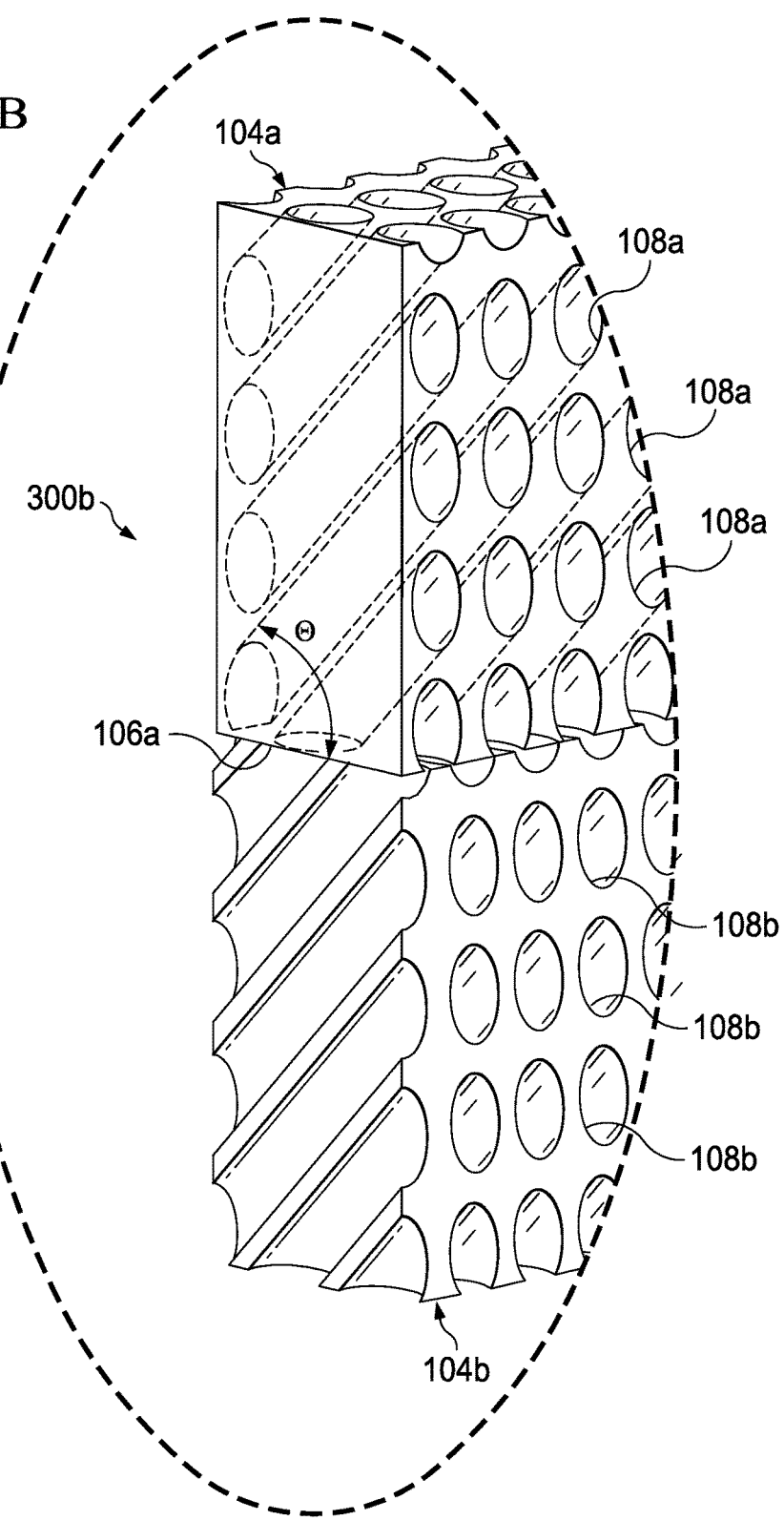

In the active cell embodiment 300b shown in FIG. 3B, active cell 104a and active cell 104b are independent structures of cell aperture arrays. The cell apertures 108a and 108b are disposed in the same transverse direction from a first side of the active cell to a second side of the active cell and are each disposed about 45 degrees (plus or minus 20 degrees) relative to a reference axis found in active cells 104.

Figure 3C:
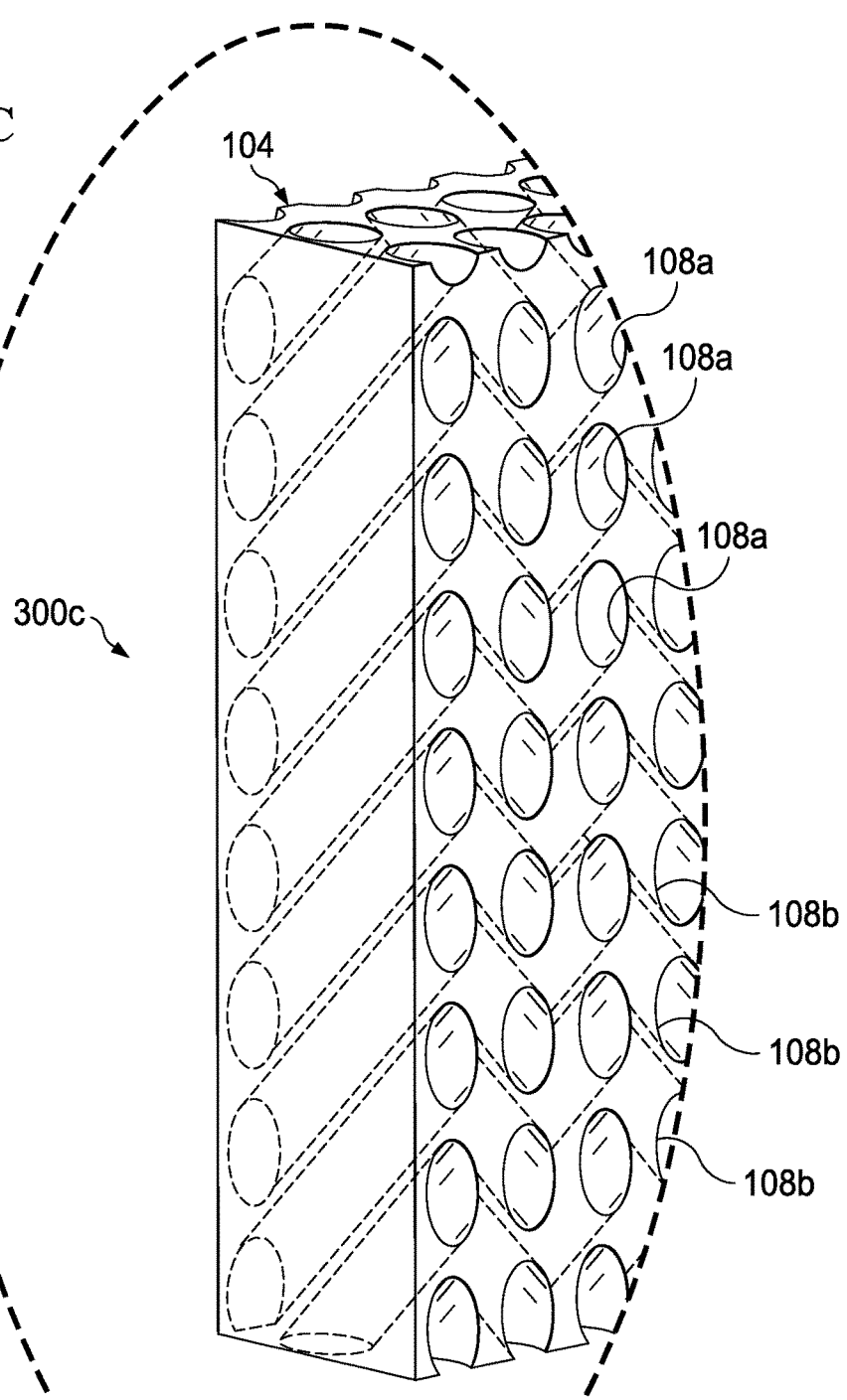

In the active cell embodiment 300c shown in FIG. 3C, active cells 104a and active cells 104b are included as a unitary structure. Columns of cell apertures 108a in active cell 104a are transversely disposed from a first side to a second side of the active cell structure at about minus 45 degrees (plus or minus 20 degrees) relative to a horizontal x-axis along a top edge of the active cell 104, while alternate columns of cell apertures 108b are transversely disposed from a first side to a second side of the active cell structure at about positive 45 degrees (plus or minus 20 degrees) relative to the horizontal x-axis long a tope edge of the active cell 104.

In the active cell 300d embodiment shown in FIG. 3D, active cell 104 is a unitary structure comprising a matrix of a plurality of cell apertures 108. Cell apertures 108 are disposed in a transverse direction from a first side of the active cell to a second side of the active cell and are disposed at about 45 degrees (plus or minus 20 degrees) relative a reference plane parallel with a front surface of the active cell 104.

In one embodiment of the present disclosure, the majority, if not all, of active cells 104 in system 100 are capable of performing a photocatalytic response to being radiated or illuminated by UV light emitted from the UV light source 202. By optimizing or maximizing the surface area of UV light exposure of the surface of the active cell 104, including the inner surfaces of the cell apertures 108, the system 200 maximizes the relative rates and amount of photocatalytic oxidation performed by the photocatalytic materials on the surfaces of the active cells 104, and thus rates of oxidation and purification of the air in the ambient environment are greater than those of conventional prior art oxidation systems, purification systems, or particle air purifiers and filters. In one embodiment, photocatalytic oxidation in system 200 could produce one or more of the following oxidizers: Hydroxyl Radicals (OH), Vaporized Hydrogen Peroxide ($H_2O_2$), Super Oxides ($O_2$—) or Low Level Ozone ($O_3$).

In one embodiment, active cell 104 could include any suitably sized and dimensioned cell apertures 108 such as, for example, cell apertures 108 that are about 55 square millimeters (mm$^2$) in volume. In other embodiments, active cell 104 could include cell apertures 108 where the average or median distance from an edge of one or more of cell apertures 108 to the center of UV light source 202 having, for example, a diameter of about 20 mm, could be about 15 mm.

Figure 4:
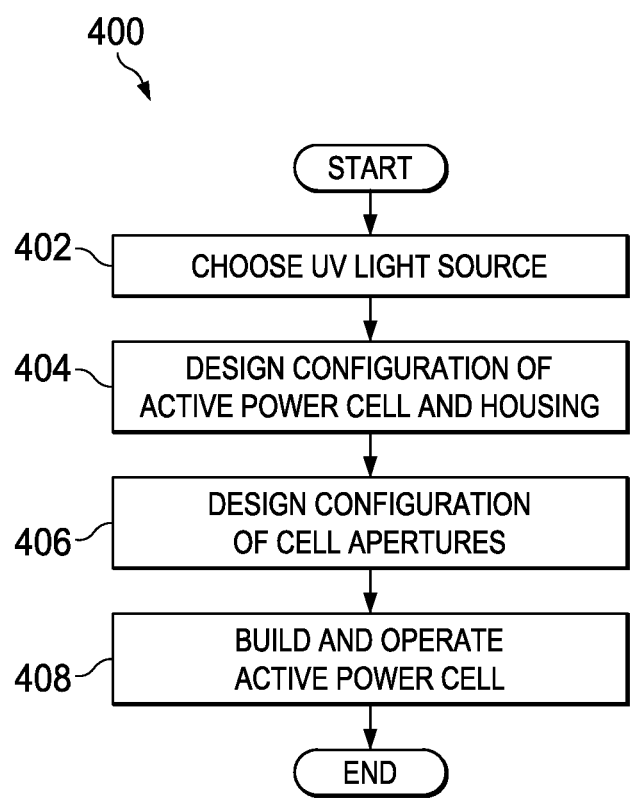
FIG. 4 is a flow diagram generally illustrating a method of using the system embodiment shown in FIGS. 1A and 1B.

FIG. 4 is a simplified flow diagram generally illustrating a method 400 of customizing and using active cell 104 shown in FIGS. 1A, 1B, 2 and 3 in accordance with an embodiment of the present disclosure. Although a particular set of steps are illustrated as method 400, it should be understood that any number of steps may be included or removed in conjunction with the steps should as method 400 or in lieu of one or more steps of method 400 according to one embodiment of the present disclosure.

In one embodiment, method 400 begins with step 402 that includes choosing a UV light source such as, for example, UV light source 202 shown in FIG. 2, of suitable size, shape and configuration for a particular photocatalytic oxidation and ambient environment oxidation and purification application.

In step 404, method 400 includes designing the configuration of an active cell and housing needed to house the UV light source chosen in step 402. As examples, the active cells could be designed to encase or substantially surround the chosen UV light source on opposing sides such as, for example, the relative positions of UV light source 202 and active cells 104 shown in FIG. 2. In another design, the system could include designing a system where the active cells are configured in a triangular fashion or circular fashion about the UV light source.

Depending on the active cell configuration chosen, step 406 may include choosing the relative angle of the cell apertures in the active cells. For example, in step 406, cell apertures 108 shown in FIG. 3, could be configured to be about 45 degrees (plus or minus 20 degrees) from a reference point such as, for example, median 106 to maximize UV exposure to the respective surfaces of active cell 104 and cell apertures 108.

Once design specifications in step 406 are complete, method 400 continues with step 408. Step 408 includes building and operating the active cell to facilitate photocatalytic oxidation and air filtration. For example, by maximizing UV exposure on the surfaces of the active cells 104, the relative rates of photocatalytic oxidation with the ambient air and thus air filtration are maximized and superior the photocatalytic oxidation rates of previous conventional oxidation system, purification systems, or particle air purifiers and filters.

Accordingly, embodiments of the present disclosure optimize or increase an active photocatalytic oxidation system increasing or maximizing the potential for ultraviolet (UV) light to impinge on the surface and apertures of the active cells, to thereby increase the rates of photocatalytic oxidation and the oxidation and purification of the ambient environment about and flowing through the inner chamber of the housing and individual apertures.

It may be advantageous to set forth definitions of certain words and phrases used in the present disclosure. The terms "ambient" and "environment" and its respective derivatives refer to any surrounding areas, air, gasses, solids, liquids, organisms, or surfaces. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith, "as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Figure 5:
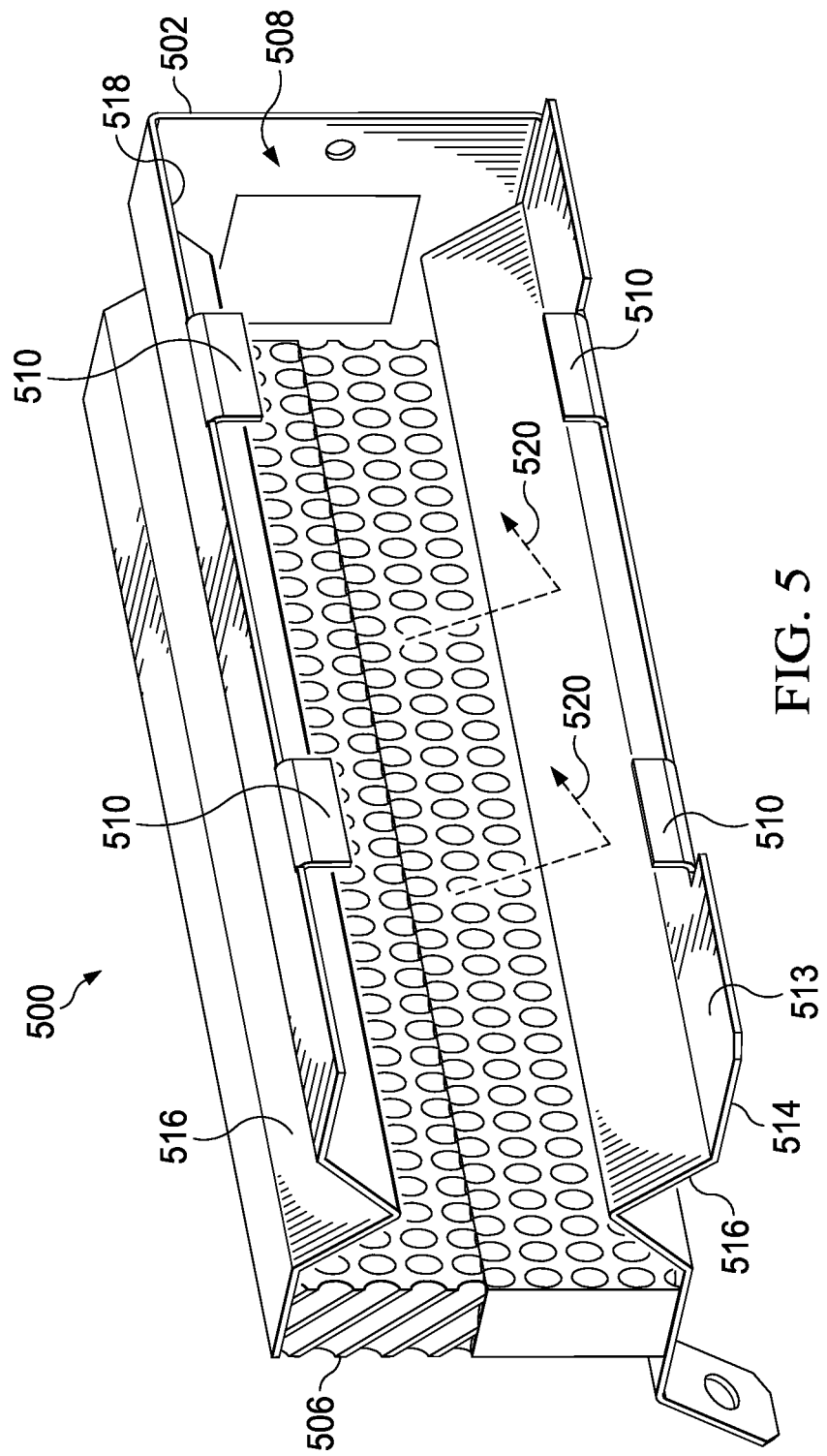
FIG. 5 is an partial exploded view of another embodiment of the active photocatalytic oxidation system

Referring now to FIG. 5, a variation of the embodiment shown in FIG. 2 is depicted. A housing 500 is shown. This housing 500 can be used in place of the housing 102 shown in FIG. 2. Housing 500 has a distal end panel 502 and a proximate end panel (not specifically shown). Two active cell panels 506 are positioned as side walls on opposing walls of the housing 500. One of the active cell panels 506 is not depicted in FIG. 5 so that the interior chamber of the housing can be viewed. The active cells 506 are held in place by retaining tabs or lips 510 extending from side edges of an upper panel 512 and lower panel 514.

When the UV light source 202 is positioned inside the interior chamber of the housing, the UV light source may be an elongated UV light source and define a longitudinal axis extending from the proximate end panel to the distal end panel 502 of the housing 500.

The upper and lower side panels 512, 514 each may extend from the proximate end panel to the distal end panel 502. The combination of the proximate end panel, distal end panel 502, the two active cell panels 506 positioned as side walls on opposing sides of the housing 500, and the upper and lower side panels each provide interior surfaces that define the interior chamber 508 of the housing 500.

On at least one of the upper and/or lower side panels 512, 514, there is a reflecting feature 516 that is configured to increase the amount of UV light directed from the UV light source 202 to the inner and cell aperture surfaces of the active cell panels 506. In some embodiments, the reflecting feature 516 comprises an inwardly convex longitudinal protrusion that extends from an inner surface portion 513 of the, for example, lower side panel 514 inward into the interior chamber 508. The convex longitudinal protrusion is elongated in the longitudinal direction of the upper side panel 512. In the embodiment shown in FIG. 5 the reflecting feature 516 extends the entire longitudinal length of the upper side panel 512. The inner surface 518 of the upper side panel 512 is reflective to UV light. In some embodiments, at least the inner surface of the reflective feature 516 is very reflective to UV light or the UV spectrum. The reflectivity of the inner surface of the upper side panel 512 may be due to the surface being buffed smooth or coated to have a reflective surface. In other embodiments, the reflectivity is due to the surface being a bare or reflective metal surface.

It should be understood that the lower side panel 514 may also include a reflective feature 516 that is similarly configured as the reflective feature 516 that is part of the upper side panel 512.

The convex longitudinal protrusion may appear like an elongated concave trough on the outside surface of the upper side panel 512. One functional purpose of the reflective feature 516 is to reflect and redirect UV light emitted from the UV light source 202 onto the upper or lower side panels 512, 514 toward the inner surface of the active cell panels 506 and the interior surfaces of the cell apertures in order to increase the photocatalytic oxidation reaction on the surfaces of the active cell panels 506 and thereby increase the efficiency and efficacy of the air, gas or liquid purification process performed by embodiments. The reflection or redirection of UV light on the surface of the reflecting feature 516 is shown by the arrows 520 indicating UV light emitted from a UV light source (not specifically shown in this figure) and being reflected and redirected toward the inner coated surfaces of the active cell panels 506. Another functional purpose of the reflective feature 516 is for the longitudinal protrusion on the upper and/or lower side panels 512, 514 to provide additional stiffening and structural support for the overall housing structure 500.

Figure 6:
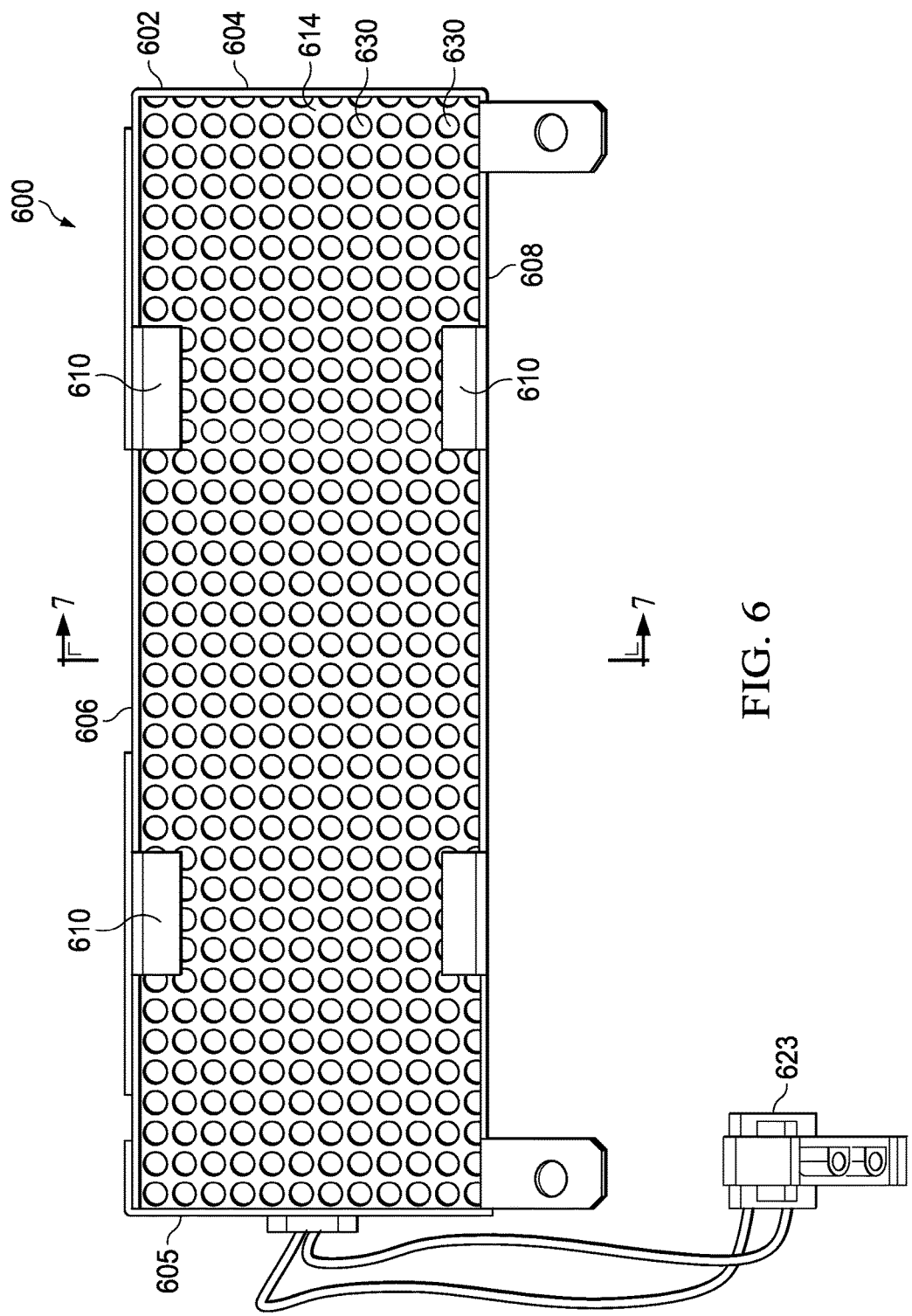
FIG. 6 is a side view of another active photocatalytic oxidation system in accordance with an embodiment of the present disclosure.
Figure 7:
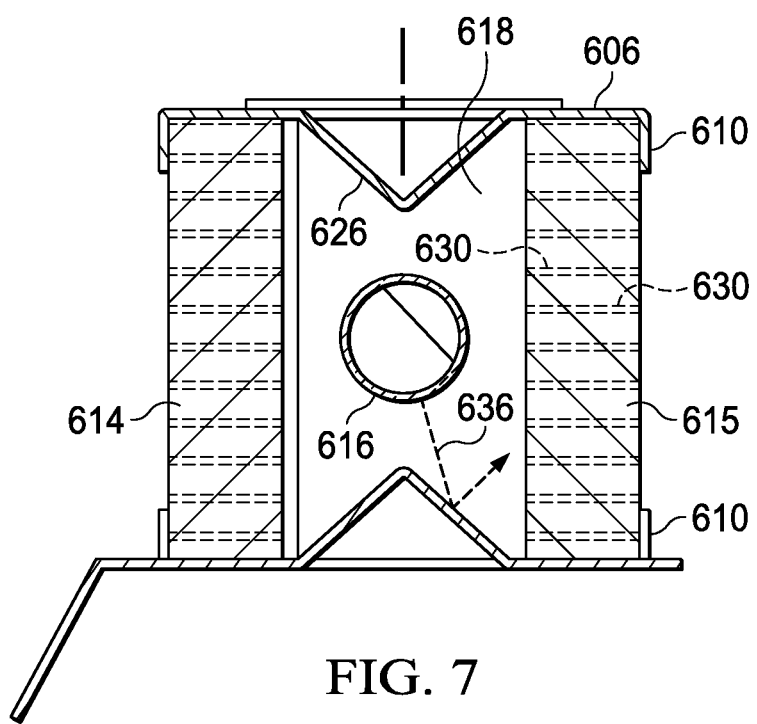
FIG. 7 is a cross sectional view of FIG. 6 along cross section line A-A.
Figure 8:
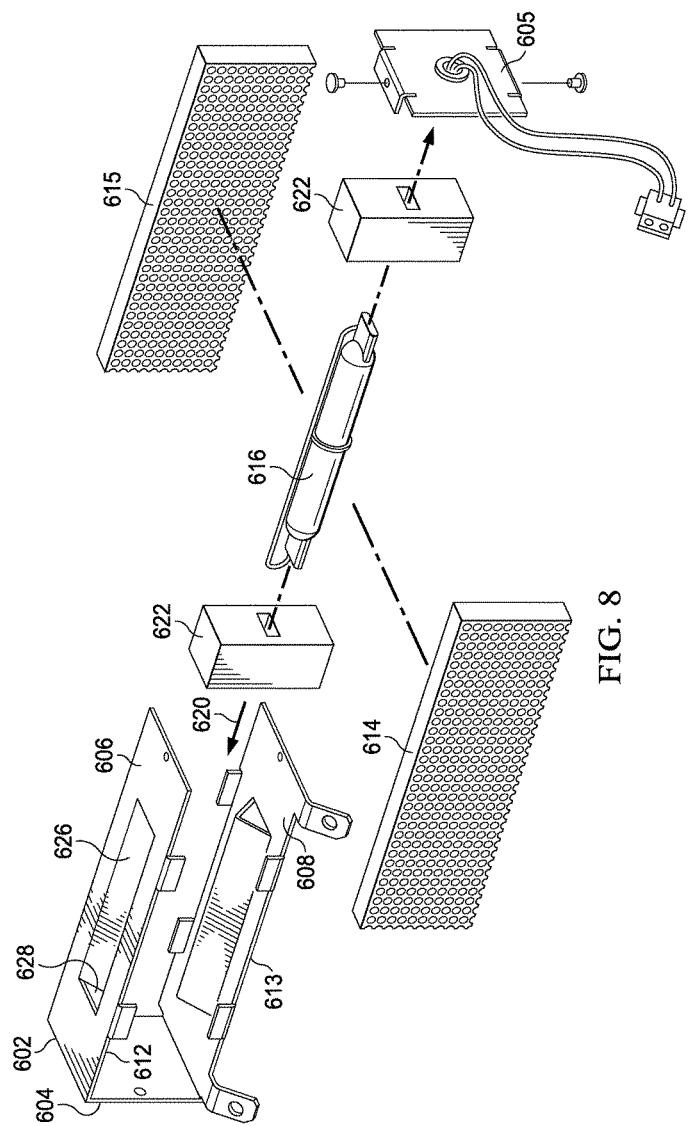
FIG. 8 is an exploded view of the active photocatalytic oxidation system of FIG. 6.

Referring now to FIGS. 6, 7 and 8 another embodiment of an active photocatalytic oxidation system 600 is disclosed. FIG. 6 is a side view of the active photocatalytic oxidation system 600. The housing 602, in this embodiment, has a distal end 604 that attaches to an upper housing portion 606 and a lower housing portion 608. The upper and lower housing portions 606, 608 extend perpendicularly from the distal end 604. The upper and lower housing portions 606, 680 are basically parallel to each other and to some degree a mirrored image of each other. The housing 602 can also be easily viewed in FIGS. 8 and 7. Along each side hedge 612 of the upper housing portion 606 are one or more retaining tabs or clips 610 that extend downwardly from the upper housing portion 606 and configured to support, position and hold a first and second active cell panel 614, 615 in place on a first side and second side of the housing 602. Similarly, along each side and 613 of the lower housing portions 608 there are one or more retaining tabs or clips 611 extend upwardly from the lower housing portions 608 and are configured to support, position hold the first and second active cell panel 614, 615 in place on the first side and second side of the housing 602.

FIG. 7 is a cross-sectional view of FIG. 6 at the cross section line A-A looking from the distal end 604 toward the proximate end 605 of the housing structure 602. Additionally, FIG. 8 is an exploded view of the active photocatalytic oxidation system 600. An elongate UV bulb 616 is positioned within a cavity 618 within the housing structure 602. The cavity 616 is defined by the inner surfaces of the upper and lower housing portions 606, 608, the first and second active cell panels 614, 615, and the proximate and distal ends 605, 604 of the housing structure 602. The elongate UV bulb 616 defines a longitudinal direction or axis 620 extending from the proximate end 605 to the distal end 604. At either end of the UV bulb 616 are support structures 622 that support the UV bulb 616. One or both of the support structures 622 have a socket or connector 624 for electrically connecting and providing power to the UV bulb 616. Although not specifically shown, there may also be an electronic circuit within one or both of the support structures 622. The electronic circuit may include a ballast circuit for a florescent UV bulb, circuitry to drive high-voltage to the UV bulb, or electronics that supports an array of ultra bright UV diodes in a ultraviolet UV bulb configuration. Electrical wires and a connector 623 may be provided to connect the UV bulb 616 to a power source. The Additionally, the upper housing portion 606 comprises a reflective feature 626, that when viewed from the cavity 618, extends in the longitudinal direction as an inwardly convex longitudinal trough. The inner surface of the inwardly convex longitudinal trough (ICLT) or reflective feature 626, is reflective or highly reflective in the UV spectrum. In some embodiments the reflective feature 626 comprises the ICLT. The reflective feature 626 may also include a UV reflective coating, buffed surface, or other additional treatment to the inner surface of the reflective feature 626. As can be easily seen in FIGS. 7 and 8, the upper housing portions 606, when viewed from the outside of the housing structure 602, has an elongated trough or indentation that extends in the longitudinal direction 620. The ICLT 626 in provides additional structural integrity and rigidity to the housing structure 602. In the embodiment shown the most inward portion of the reflective feature 626 is disposed in a plane or is centered with a longitudinal axis of the elongate UV bulb 616. In various embodiments the ICLT reflective feature 626 appears like a trough on the outside of the upper housing portion 606 and appears like an elongated protrusion into the cavity 618 on the inside of the upper housing portion 606. In this embodiment the reflective feature does not extend the full longitudinal distance between the proximate end 605 and distal end 604. Instead, a gap or airway 628 is established at either end of the reflective feature 626, which allows for additional airflow between the outside environment of the housing structure 602 end the inner cavity 618.

When the UV bulb 616 is on and emitting ultraviolet light, the inside surfaces of the reflective feature 626 reflects ultraviolet energy emitted from the UV bulb 616 that is directed toward the inner surfaces of the upper housing portion 606 directly toward the surfaces (i.e., inner surfaces) of the active cell panels 614, 615 and the respective inner surfaces of the cell apertures 630 that make up the active cell panels 614, 615 (for example as shown by the arrow 632 in FIG. 7. It is been found that providing the reflective feature 626 in the upper housing portion 606, the efficiency and effectiveness of an active photocatalytic oxidation system 600 is increased over a system that does not include the reflective feature 626.

In various embodiments, the reflective feature 626 is also incorporated or included in the lower housing portion 608 in a manner similar to the description above with respect to the upper housing portion 606 and as shown in FIGS. 6, 7 and 8.

In other embodiments the reflective feature 626, when viewed in cross-section such as the cross-sectional view A-A perpendicular to the longitudinal axis, may have any convex shape, including but not limited to, a V-shape as show, a half circle, half oval, half octagon or other multi-sited or faceted shape that provides a mirrored image of itself about a central longitudinal vertical plane 917 through the trough (shown as dotted lines).

Figure 9:
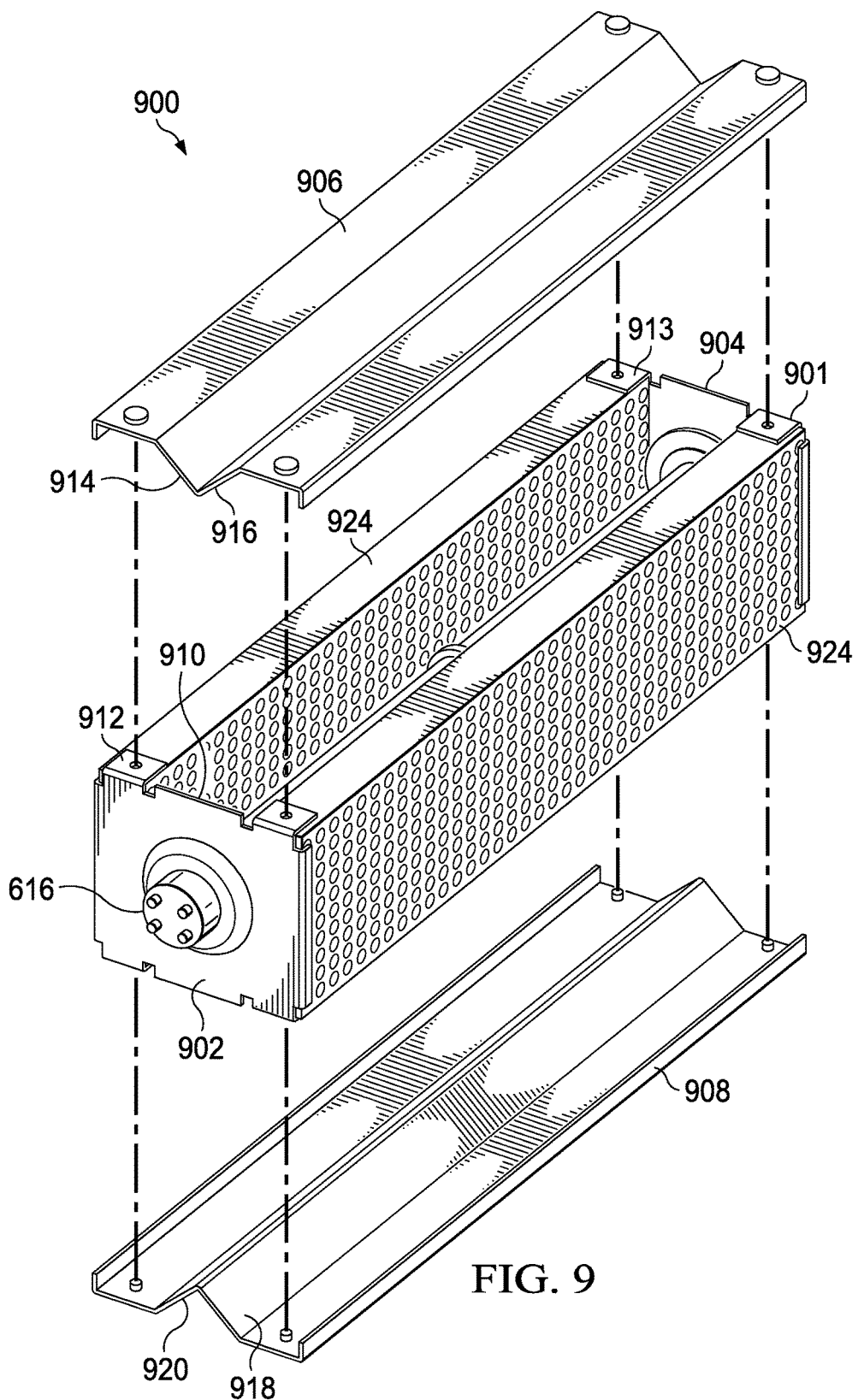
FIG. 9 is an exploded view of another embodiment of an active photocatalytic oxidation system.
Figure 10:
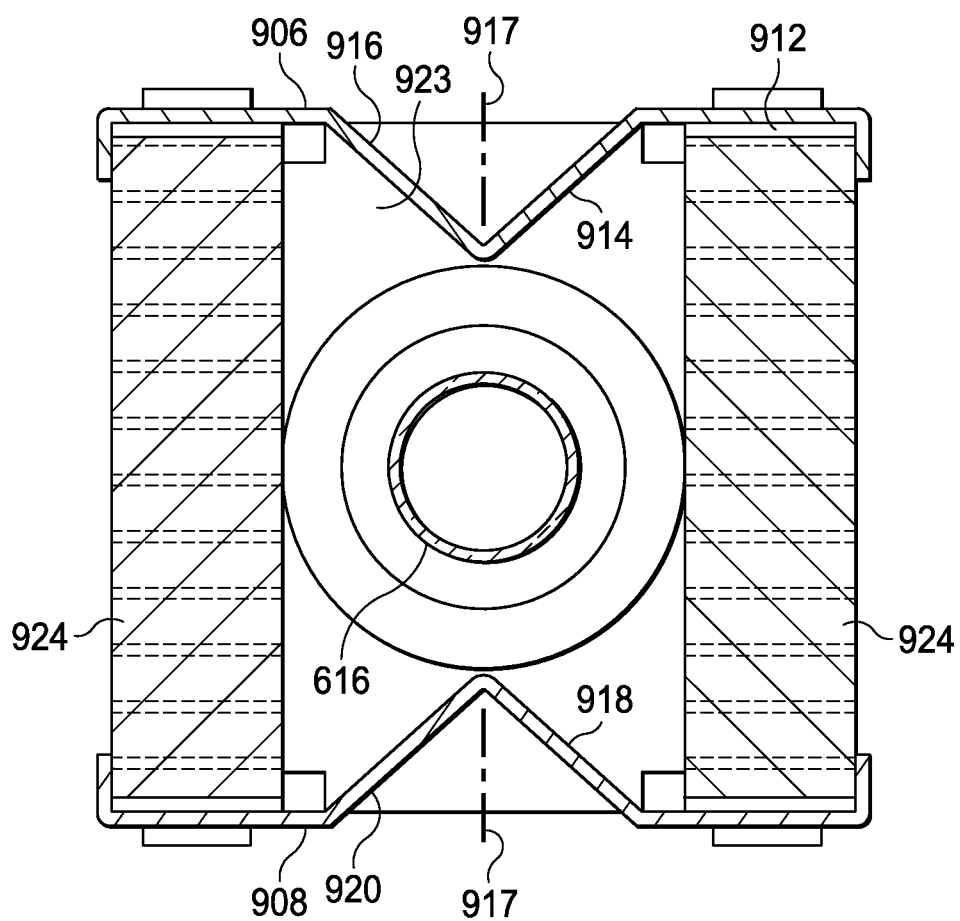
FIG. 10 is a cross section view of the assembled embodiment of FIG. 9 taken perpendicular to a longitudinal axis of the embodiment.

Referring now to FIG. 9 an exploded view of yet another embodiment of an active photocatalytic oxidation system 900 is provided. Additionally, FIG. 10 is a cutaway view perpendicular to the longitudinal direction of the assembled system 900. In this embodiment, the system 900 has a housing 901 having a proximate end panel 102, a distal end panel 904. An upper panel 906 and lower panel 208 extend parallel to each other. The upper panel 906 removably attaches to an upper edge 910 or upper tabs 112 of the proximate end panel 902. The upper panel 906 extends in a longitudinal direction from the upper edge 910 of the proximate end panel 902 to the upper edge 910 of the distal end panel 904 where it is also removably attached to upper tabs 913.

The upper panel 906 comprises a reflective feature 914 extending the longitudinal length of the upper panel 906. The reflective feature 914, on the inner surface of the upper panel 906, includes an inwardly convex longitudinal trough (ICLT) 916 that extends into the interior of the housing 901. The inner surface of the ICLT reflective feature 914 is reflective or highly reflective to the UV spectrum. In this embodiment, the ICLT reflective feature, from the outside of the housing 901, looks like a concave trough extending longitudinally from a proximate to a distal end of the upper panel 906. The ICLT reflective feature 914 looks like a convex longitudinal trough with a reflective surface that extends inwardly into the cavity 923 of the system housing 901.

The lower panel 908 also comprises a reflective feature 918 that extends the longitudinal length of the lower panel 908. On the inner surface of the lower panel 908, the reflective feature 918 includes an inwardly convex longitudinal trough (ICLT) 920 that extends into the interior of the housing 901. Like the inner surface of the ICLT reflective feature 914, the ICLT reflective feature 918 is reflective or highly reflective to the ultraviolet spectrum. From the outside of the housing, the ICLT reflective feature 918 looks like a concave trough extending longitudinally from a proximate to a distal end of the lower panel 906. Furthermore the ICLT reflective feature 918 looks like a convex longitudinal trough with a reflective surface that extends inwardly into the cavity 923 of the system housing from the perspective of inside the system housing 901. In cross-section, the reflective features 914, 918 may be a V-shape, half circle, half oval, half hexagon or half any other faceted or multi sided shape that is mirrored about a feature's central longitudinal vertical plane 917 (shown as a dotted line).

The elongate UV bulb 922 is positioned to extend longitudinally between the proximate end panel 902 and the distal end panel 904. In some embodiments, the proximate end panel 902 and/or distal end panel 904 may each include a centrally located mechanism for holding the UV bulb 922 such that it maintains a central position within the inner cavity 923 of the housing 901. In various embodiments the upper and lower reflective features 914, 918 have a longitudinal center line that is parallel with a longitudinal axis of the UV bulb 922.

On opposing sides of the housing 901 are opposing active cell panels 924 that each extend from opposing sides of the proximate end panel 9022 opposing sides of the distal end panel 904. The tabs 912 of the proximate end panel 902 and the tabs 914 of the distal end panel 904 are used to attach the upper panel 906, the two active cell panels 924, the lower panel 908 and the proximate end panel 902 and distal end panel 904 together so as to establish the inner cavity 923 of the housing 901.

The high sea LTE reflective features 914, 918 provide structural stabilizing support for the housing 901 as well as the reflective surface on the inside sides of the upper and lower panels 906, 908 that increases the amount of ultraviolet light directed toward the inside surfaces of the active cell panels 924 as well as the inside surfaces of the cell apertures comprised within the active cell panels 24. UV light emitted toward the upper or lower panels is reflected by the reflective features 914, 918 directly toward the various active surfaces associated with the active cell panels on either side of the housing 901.

The UV bulb 616 the have a connector at one or both ends of the housing for connecting to electrical power.

During operation, the UV bulb 616 emits UV light radiation radially from the longitudinal axis of the UV bulb. Much of the UV radiation impinges directly upon various inner surfaces of the active side panels. Much of the UV radiation also impinges on the inner surfaces of the upper and lower panels 906, 908. The reflective features 914 and 918 on the upper and lower panels increase the amount of UV light intensity that is directed onto the inner surfaces of the active side panels so as to increase the amount or efficiency of the photocatalytic oxidation reaction that occurs on the surfaces of the active panels. Gases or air may flow or be forced to flow through the apertures that make up the active panels such that bacteria, pathogens and other airborne items may be oxidized in the purification process as a result of the reaction occurring between the ultraviolet light and the photocatalytic materials, such as titanium dioxide and other compounds that could hold the surfaces of the active cell panels 924. By slanting or placing the individual cell apertures at an angle with respect to the horizontal, the surface area inside of the apertures that is impinged by UV light is be increased, especially with the angled reflection of the UV light off of the reflective features 914, 918.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure and the following claims.

What is claimed is:
1. A photocatalytic oxidation system comprising:
a housing comprising:
a proximate end panel;
a distal end panel, the housing having a longitudinal direction extending from the proximate end panel to the distal end panel;
an upper panel between top sides of both the proximate end panel and the distal end panel; and
a lower panel between lower sides of both the proximate end panel and the distal end panel, the lower panel being spaced from the upper panel;
a first active cell panel positioned between a first side of the proximate end panel, a first side of the distal end panel, a first side of the upper panel, and a first side of the lower panel; the first active cell panel comprises a first plurality of apertures disposed in a first transverse manner from an inner side to an outer side of the first active cell panel, each aperture of the first plurality of apertures has a first aperture surface, wherein the first transverse manner of the first set of apertures comprises a relative disposition of about 20-70 degrees from the inner side, wherein the inner side and the first aperture surfaces of each aperture of the first plurality of apertures are coated with a photocatalytic material;
a second active cell panel positioned between a second side of the proximate end panel, a second side of the distal end panel, a second side of the upper panel, and a second side of the lower end panel; the second active cell panel comprising a second plurality of apertures disposed in a second transverse manner from an inner side to an outer side of the second active cell panel;
an interior chamber bounded by the proximate end and distal end panels, the upper and lower panels, and the first and second active cell panels;
an elongate UV bulb positioned inside the interior chamber and having a center axis that is parallel with the longitudinal direction; and
a first reflective feature that protrudes inward into the interior chamber from an inner surface of the upper panel, the first reflective feature extends in the longitudinal direction on the inner surface of the upper panel and is configured to reflect ultraviolet (UV) radiation emitted radially from the elongate UV bulb toward the first plurality of apertures and the inner side of the first active cell, as well as toward the second plurality of apertures and the inner side of the second active cell.

2. The system of claim 1, wherein the first reflective feature further comprises a convex protrusion into the interior chamber from the inner surface of the upper panel.

3. The system of claim 2, wherein the reflective feature is a V-shape in cross section.

4. The system of claim 1, wherein the first reflective feature is further configured to provide stiffening and structural support to the housing.

5. The system of claim 1, wherein the first reflective feature extends a portion of an entire longitudinal length of the upper panel and further comprises an airway gap at a first end of the reflective feature, the airway gap configured to allow airflow to or from the interior chamber.

6. The system of claim 1, wherein a center longitudinal axis of the first reflective feature is aligned with the center axis of the elongate UV bulb.

7. The system of claim 1, wherein the reflective feature comprises a metal UV reflective surface.

8. The system of claim 1, further comprising a second reflective feature that protrudes inward into the interior chamber from an inner surface of the lower panel, the second reflective feature extends in the longitudinal direction on the inner surface of the lower panel and is configured to reflect UV radiation emitted radially, from the elongate UV bulb toward the lower panel, toward the first plurality of apertures and the inner side of the first active cell, as well as toward the second plurality of apertures and the inner side of the second active cell.

9. The system of claim 8, wherein the second reflective feature is further configured to provide stiffening and structural support to the housing.

10. A photocatalytic oxidation system comprising:
 a housing comprising:
  a proximate end panel;
  a distal end panel, the housing having a longitudinal direction extending from the proximate end panel to the distal end panel;
  an upper panel between top sides of both the proximate end panel and the distal end panel;
  a lower panel between lower sides of both the proximate end panel and the distal end panel, the lower panel being spaced from the upper panel;
 a first active cell panel positioned between a first side of the proximate end panel, a first side of the distal end panel, a first side of the upper panel, and a first side of the lower panel; the first active cell panel comprises a first plurality of apertures disposed in a first transverse manner from an inner side to an outer side of the first active cell panel, each aperture of the first plurality of apertures has a first aperture surface, wherein the inner side and the first aperture surfaces of each aperture of the first plurality of apertures are coated with a photocatalytic material;
 a second active cell panel positioned between a second side of the proximate end panel, a second side of the distal end panel, a second side of the upper panel, and a second side of the lower end panel; the second active cell panel comprising a second plurality of apertures disposed in a second transverse manner from an inner side to an outer side of the second active cell panel;
 an interior chamber bounded by the proximate end and distal end panels, the upper and lower panels, and the first and second active cell panels;
 an elongate UV bulb positioned inside the interior chamber and having a center axis that is parallel with the longitudinal direction; and
 a first reflective feature integral to the upper panel protrudes inward into the interior chamber from the upper panel forms a trough on a second side of the upper panel, the first reflective feature extends in the longitudinal direction of the upper panel and is configured to reflect ultraviolet (UV) radiation emitted radially from the elongate UV bulb toward the first aperture surfaces and the inner side of the first active cell, as well as toward the second plurality of apertures and the inner side of the second active cell, wherein the first reflective feature extends a portion of an entire longitudinal length of the upper panel and further comprises an airway gap at a first end of the reflective feature, the airway gap configured to allow airflow to or from the interior chamber.

* * * * *